United States Patent [19]

Griffing et al.

[11] Patent Number: 5,108,874

[45] Date of Patent: Apr. 28, 1992

[54] COMPOSITE USEFUL IN PHOTOLITHOGRAPHY

[75] Inventors: Bruce F. Griffing, Schenectady; Paul R. West, Clifton Park, both of N.Y.

[73] Assignee: MicroSi, Inc., Phoenix, Ariz.

[21] Appl. No.: 398,316

[22] Filed: Aug. 23, 1989

Related U.S. Application Data

[60] Continuation of Ser. No. 937,953, Dec. 4, 1986, abandoned, which is a division of Ser. No. 675,915, Nov. 28, 1984, Pat. No. 4,677,049, which is a division of Ser. No. 536,923, Sep. 28, 1983, abandoned, which is a continuation-in-part of Ser. No. 438,194, Nov. 1, 1982, abandoned.

[51] Int. Cl.$^5$ .......................... G03F 7/095; G03C 1/72
[52] U.S. Cl. .................................... 430/273; 430/339; 430/396; 430/312; 430/272; 430/156; 430/509; 430/502
[58] Field of Search ............... 430/273, 339, 396, 312, 430/272, 156, 509, 502, 312

[56] References Cited

U.S. PATENT DOCUMENTS

| | | | |
|---|---|---|---|
| 2,426,894 | 9/1947 | McQueen | 430/337 |
| 3,416,922 | 12/1968 | Sus et al. | |
| 3,511,653 | 5/1970 | Wiebe | 430/5 |
| 3,925,077 | 12/1975 | Lewis et al. | |
| 3,965,278 | 6/1976 | Duinker et al. | 430/23 X |
| 4,025,191 | 5/1977 | Seward, III | 355/71 |
| 4,411,978 | 10/1983 | Laridon et al. | 430/157 |

FOREIGN PATENT DOCUMENTS

| | | |
|---|---|---|
| 0161660 | 11/1985 | European Pat. Off. |
| 2384284 | 10/1978 | France |
| 52-130286 | 11/1977 | Japan |
| 54-64971 | 5/1979 | Japan |
| 54-70761 | 6/1979 | Japan |
| 2000169 | 1/1979 | United Kingdom |

OTHER PUBLICATIONS

H. J. Zweig, "Nonlinear Filter", IBM Technical Disclosure Bulletin, vol. 8, No. 7, Dec., 1965, p. 980.
Jaromir Kosar, Light-Sensitive Systems: Chemistry and Application of Nonsilver Halide Photographic Processes, John Wiley & Sons, Inc., New York, 1965, pp. 269-270.
Skoog and West, "Fundamentals of Analyic Chemistry", 2nd Ed., 1969, pp. 644-652.
"Methoden der Organischen Chemie", (Houben-Weyl), vol. 10, part 4, 1968, pp. 315-416.
Hamer and Macaluso, "Nitrones", Chemical Reviews, 1964, pp. 476-483.

Primary Examiner—Cynthia Hamilton
Attorney, Agent, or Firm—Davis Hoxie Faithfull & Hapgood

[57] ABSTRACT

The image of an object with opaque and transparent regions having a contrast less than the contrast threshold of a layer of photoresist when light of a predetermined wavelength to which the photoresist is sensitive is passed through the object and onto the layer of photoresist is enhanced in contrast by the provision of a contrast enhancing layer contiguous to the surface of the photoresist to a value above the contrast threshold of the photoresist. The contrast enhancing layer is constituted of an aryl nitrone compound mixed with a suitable binder.

8 Claims, 3 Drawing Sheets

COMPOSITE USEFUL IN PHOTOLITHOGRAPHY

This application is a continuation of application Ser. No. 937,953, filed Dec. 4, 1986, now abandoned, which is a division of application Ser. No. 675,915filed Nov. 28, 1984, now U.S. Pat. No. 4,677,049; which is a division of Ser. No. 536,923, filed Sep. 28, 1983, now abandoned which is a continuation-in-part of Ser. No. 438,194, filed Nov. 1, 1982, now abandoned.

The present invention is directed to a method of enhancing the contrast of images of objects such as masks for photolithography in the manufacture of integrated circuits and materials therefor.

Lithography in the production of integrated circuits is predominantly carried out by optical means. In the drive to reduce circuit dimensions, improve performance and increase yield, optical systems have provided the required resolution with each successive generation of circuit technology. The image resolution of projection lithographic systems has recently begun to approach the physical limits imposed by practical constraints on numerical aperture and wavelength. While further improvements in lithographic technology are anticipated, dramatic improvements in inherent lens resolution are not. In order to continue the reduction of minimum feature size achievable by optical techniques, it is necessary to alter some other aspect of the lithographic process for further improvements. One area in which further improvements are possible is in the photoresist process. Each photoresist is characterized by some degree of incident contrast necessary to produce patterns usable for subsequent processing. This minimum required contrast of illumination is referred to as the contrast threshold of the resist. Depending on substrate properties, the required pattern thickness and resist edge profiles, conventionally used positive photoresist has a contrast threshold between 85% and 90% contrast. Currently, most production is done at 90% incident contrast or more. If the contrast threshold of the resist is reduced, the resolution obtainable with a given optical system is improved due to the fact that image contrast is a decreasing function of the spatial frequencies present in the image.

The present invention is directed to provide a photoresist process in which the contrast of an aerial image utilized in the process is enhanced prior to incidence on the photoresist.

An object of the present invention is to lower the minimum contrast required to produce usable images in a photoresist.

Another object of the present invention is to provide new photobleachable compounds and materials.

In carrying out the invention in an illustrative embodiment thereof, a layer of photoresist of a first thickness and having a predetermined contrast threshold is provided. An object or mask is provided having opaque and transparent areas. An image having a contrast less than the predetermined contrast threshold of the photoresist is formed of the object on the layer of photoresist by projecting light of a predetermined wavelength through the object. A layer of photobleachable material including a photobleachable compound is provided between the object and the layer of photoresist and adjacent a surface of the layer of photoresist. The photobleachable compound is sensitive to the aforementioned wavelength of light and has an extinction coefficient to molecular weight ratio in liters per gram-centimeter in the unbleached state greater than about 10. The ratio of the extinction coefficient for the unbleached state to the extinction coefficient for the bleached state of the photobleachable material is also greater than about 10. Light of the aforementioned wavelength and of a predetermined intensity is projected through the object onto the layer of photobleachable material for a time to obtain a reduction in optical density of the layer of photobleachable material in direct proportion to the dosage of light of the aforementioned wavelength incident thereof, whereby the integrated contrast of the image transmitted by the layer of photobleachable material increases with dosage transmitted thereby, reaches a maximum value and thereafter decreases. Parameters of the layer of photobleachable material are selected such that the maximum value of integrated contrast is greater than the predetermined threshold contrast of the layer of photoresist. The sensitivity of the layer of photoresist and the thickness thereof are selected such that the layer of photoresist is fully exposed by a dosage in a predetermined range transmitted by the layer of photobleachable material and provides an integrated contrast in the transmitted image above the predetermined contrast threshold of the photoresist. Light of the aforementioned predetermined wavelength is projected through the object for a time to provide the dosage in aforementioned predetermined range transmitted through the photobleachable layer. The layer of photobleachable material is removed and the layer of photoresist is developed whereby a pattern representing an enhancement in contrast of the image of reduced contrast of the object is formed in the layer of photoresist.

Another aspect of the present invention is directed to a spin castable mixture capable of forming a photobleachable layer having an absorption maximum in the range of 300 to 450 nanometers comprising by weight
(A) 100 parts of organic solvent,
(B) 1 to 30 parts, preferably 5 to 15 parts, of an inert organic polymer binder,
(C) 1 to 30 parts, preferably 5 to 15 parts, of an aryl nitrone.

The novel features which are believed to be characteristic of the present invention are set forth with particularity in the appended claims. The invention itself, both as to its organization and method of operation, together with further objects and advantages thereof may best be understood by reference to the following description taken in connection with the accompanying drawings wherein:

Figure 1:
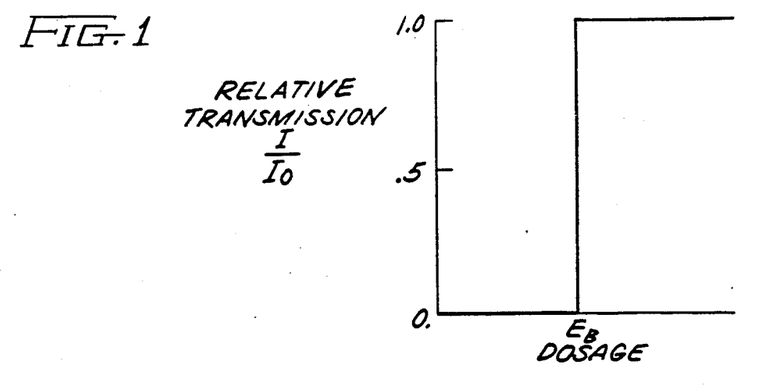
FIG. 1 is a graph showing the relative transmission of an idealized bleachable layer as a function of dosage applied to an entrance surface thereof.

A large fraction of optical lithography is done currently by projection techniques in which an aerial image of a mask is used to expose the photoresist. For an aerial image of low contrast, even those parts of the image that correspond to the dark regions of the mask have significant intensities. As the contrast is reduced, discrimination of the darker area from the lighter area becomes increasingly difficult. In accordance with the present invention a method is provided which enhances the contrast of the image incident on the photoresist and thereby improves this discrimination. The contrast enhancement is based on the use of photobleachable materials which are initially relatively opaque, but following some dose of radiation, become relatively transparent. The optical transmission of an idealized bleachable layer is shown in FIG. 1. When the aerial image of a mask is incident on such a layer, the regions of the bleachable layer that are exposed to the highest intensities bleach through first, while those parts of the layer that receive the lowest intensities bleach through at a later time.

Figure 2A:
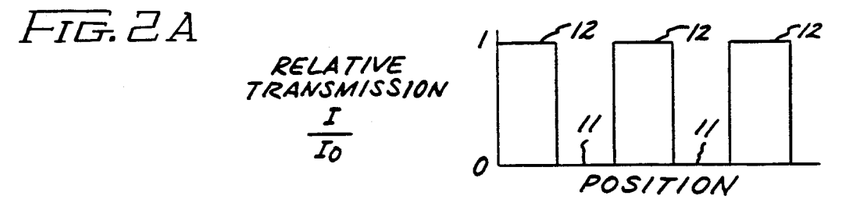
FIGS. 2A-2F show diagrams useful in explaining the dynamics of the bleaching process used in the present invention.
Figure 2B:
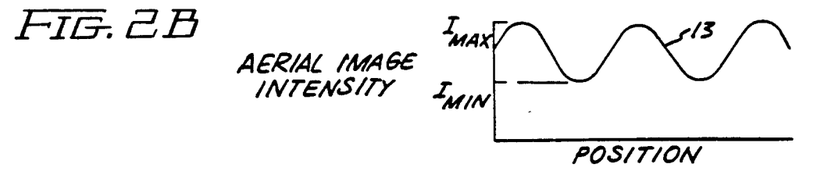
Figure 2C:
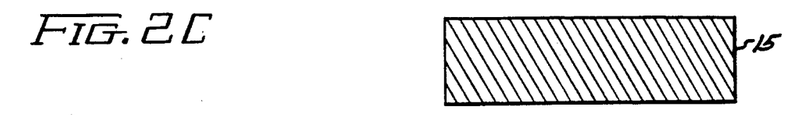
Figure 2D:
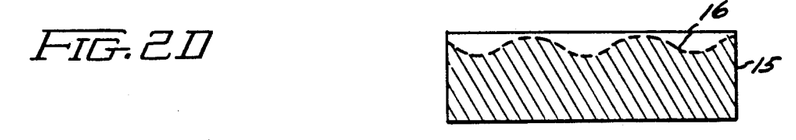
Figure 2E:
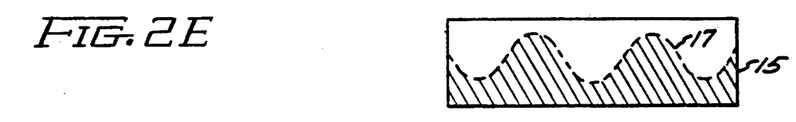
Figure 2F:
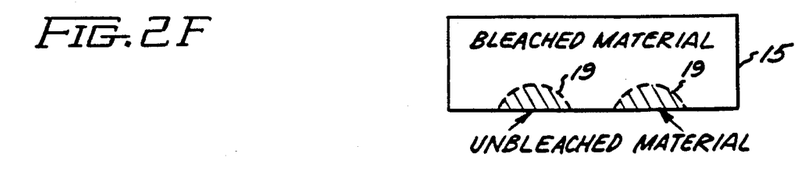

The dynamics of this bleaching process are depicted in FIGS. 2A-2F. FIG. 2A shows the relative transmission of an object such as a mask consisting of opaque regions producing zero transmission 11 separated by open or transparent regions producing 100% transmission 12. $I_o$ is incident intensity of radiation. I is transmitted intensity of radiation. $E_b$ is the dosage of radiation required to cause bleaching of the layer. FIG. 2B shows a graph 13 of the relative intensity as a function of position of an aerial image of the mask when placed in optical projection apparatus for producing an aerial image used, for example, for exposure of a layer of photoresist. It is assumed that the wavelength of light used and the dimensions of the regions of the mask are such as to produce the contrast shown. $I_{max}$ is the maximum intensity of the image and $I_{min}$ is the minimum intensity of the image. FIG. 2C shows the cross-section of a layer 15 of an idealized photobleachable material. FIG. 2D shows the bleaching of the layer 15 as delineated by the dotted line 16 at the end of a first period of time. FIG. 2E shows the bleaching of the layer 15 as delineated by dotted line 17 at a later period of time. FIG. 2F shows the bleaching of the layer 15 as delineated by dotted lines 18 and 19 at the time the exposure is terminated and bleaching stopped. If the exposure is stopped at a time corresponding to FIG. 2F, the transmission of the bleachable layer corresponds to that of the original mask. When such a material is coated on top of a conventional photoresist layer, the resulting composite can have lower contrast threshold than the contrast threshold of resist layer alone. This will be true if the photoresist is sensitive enough to be exposed in a time short compared to the bleaching time. The bleachable layer essentially forms an in situ contact mask for the photoresist layer. The net effect of this in situ mask is to increase the contrast which is incident on the photoresist over the contrast of the aerial image.

The application of contrast enhancing techniques to submicron optical lithography raises several physical and chemical constraints on the contrast enhancing layer itself. The contrast enhancing layer must be simultaneously thin and optically dense. The thickness requirement arises because of the narrow depth of focus of high resolution optical systems. This limits the thickness to a range of less than about 1 micron. Because the contrast enhancing layer must be optically dense, it is necessary that the photochemical constituent of the layer be strongly absorbing. Since the optical transmission following bleaching is determined by the absorption of photoproducts, the photoproducts must have a much smaller extinction coefficient than the parent molecule. Extinction coefficient is defined by the equation $$\epsilon = \frac{A}{bc}, \quad (1)$$

where
A is absorbance,
b is path length (cm.), and
c is concentration (mole per liter).
Absorbance is defined by equation $$A = \log_{10} \frac{I_o}{I}, \quad (2)$$

where
$I_o$ is intensity of incident radiation, and
I is intensity transmitted radiation.

The extinction coefficient $\epsilon$ of a material is obtained by determining the parameters A, b and c in equation (1). The parameter A is obtained from equation (2). Initially, a known amount of a material by volume is dissolved in a known amount of a solvent by volume to obtain the concentration c of the material in the solution. This solution is put into a cell of known dimensions and placed in the light path of a spectrophotometer and radiation of known intensity $I_o$ is directed onto the cell. The intensity of the radiation transmitted from the cell is measured. The solvent alone is also put into another cell of the same known dimensions and placed in the light path of the spectrophotometer and radiation of known intensity $I_o$ is directed onto the cell. The intensity of the radiation transmitted from the cell is measured. The intensity measurements of solvent alone is used to correct the transmitted intensity I for cell and solvent absorption. Thus using these values of incident intensity $I_o$ and transmitted intensity I in equation (2), absorbance A is obtained. Dimension b is obtained from the cell of known dimensions. Thus, the extinction coefficient for the material is obtained by substitution of values b, c and A in equation (1). The measurement of the extinction coefficients of materials is also described on pages 644-652 in "Fundamentals of Analytic Chemistry", 2nd Edition (1969) by Douglas A. Skoog and Donald M. West, published by Hold, Rinehart and Winston, Inc. of New York, N.Y. Continuing, in order to minimize the necessary increase in exposure time, the quantum yield of the bleaching reaction must be as high as possible. Also, since photoresists are conventionally applied by spin coating techniques, it would be convenient if the contrast enhancing layer could also be applied by similar methods. The solvent in which the bleachable material is dissolved must be compatible with photoresist layers. Further, it is required that it be possible to spin coat contrast enhancing layers of good optical quality. Finally, the wavelength range over which these bleachable materials operate must be the same as the wavelength range over which the optical projection system operates. Most direct-step-on-the-wafer systems operate at 405 nm (nanometers) or 436 nm. In this case, the 405 nm wavelength was chosen for use on an Optimetix 10:1 DSW system available from Optimetrix Co. of Mountain View, Calif. The search for appropriate bleaching materials was made with regard to these constraints. Particularly, the search for appropriate bleaching materials was made with regard to absorption maxima in the wavelength range of 300 to 450 nanometers.

A model of the bleaching process was developed and utilized in the evaluation of bleachable materials suitable for use in the contrast enhancing layer. The parameters of the model are set forth in the following table:

TABLE 1

| Quantity | Explanation |
|---|---|
| $\epsilon_A$ | Extinction coefficient of unbleached molecules |
| $\epsilon_B$ | Extinction coefficient of bleached molecules |
| $\Phi$ | Quantum yield of the bleaching reaction |
| $N_o$ | Initial density of unbleached molecules |
| $F_o$ | Flux density of photons incident on contrast enhancing layer |
| $t_o$ | Thickness of contrast enhancing layer |
| $n_f$ | Index of refraction of bleached layer |
| $n_s$ | Index of refraction of glass substrate on which the contrast enhancing layer is situated |

Based on the analysis above and the model of the bleaching process three criteria for material parameters were developed and are set forth in Table 2.

TABLE 2

| | Quantity | Value |
|---|---|---|
| (1) | $\epsilon$/Molecular Weight | $\gtrsim 100$ liters/gram-cm |
| (2) | $\Phi$ | $\gtrsim 0.2$ |
| (3) | $\dfrac{\epsilon_{unbleached}}{\epsilon_{bleached}}$ | $\gtrsim 30$ |

The first criterion is based on the need for an optically dense film, and is essentially related to the packing density of absorbing centers in the contrast enhancing layer. The second criterion is based on the need for as abrupt a transition from the unbleached to the bleached state as is possible. Acceptability of a given quantum yield is to some extent related to the first criterion, because improvements in the first can compensate for deficiencies in the second criterion. The third criterion is based on the need for the contrast enhancing layer to be transparent following the bleaching process. These criteria were used in the initial search for appropriate bleachable materials.

Selection of suitable bleachable compound was determined by evaluation in the model of the bleaching process and by test of the compound in a layer thereof to determine the relative transmission as a function of time or dosage of radiation with radiation intensity being held constant. A number of different bleachable compounds, the bleaching properties of which were based on different bleaching mechanisms were evaluated. The bleachable compounds dependent on photoisomerization were found to be particularly suitable. Of these compounds, aryl nitrones represented by formula 1, were found particularly suitable.

In formula 1 Z is a monovalent group selected from $(R^3)_a$-Q-$R^4$- or $R^5$- and Z' is a monovalent group selected from -$R^6(X)_b$, R, $R^1$, $R^2$ and $R^3$ are monovalent radicals selected from the class of hydrogen, $C_{(1-8)}$ alkyl, $C_{(1-8)}$ substituted alkyl, $C_{(6-13)}$ aryl hydrocarbon and $C_{(6-13)}$ substituted aryl hydrocarbons. Q is a monovalent divalent or trivalent atom selected from the group F, C, Br, I, O, S, N, where a can have values of 0, 1 or 2. $R^4$ is a $C_{(6-13)}$ aryl hydrocarbon or a $C_{(6-13)}$ substituted aryl hydrocarbon. $R^5$ is selectable from the group of substituted or unsubstituted $C_{(6-20)}$ aromatic heterocyclic compounds incorporating one or more atoms from the group O, N or S. $R^6$ is selected from the group of $C_{(6-20)}$ aromatic hydrocarbons and X is selected from the group of halo, cyano, alkyl carbonyl, $C_{(1-8)}$ alkyl, $C_{(1-8)}$ substituted alkyl, $C_{(6-13)}$ aryl hydrocarbon, $C_{(6-13)}$ substituted aryl hydrocarbons, or alkoxy carbonyl in any combination for values of b of 0, 1, 2 or 3. n can have values of 0, 1, 2, 3 or 4. The above compounds can be prepared using procedures such as those described in "Methoden der Organischen Chemie (Houben-Weyl), Vol. 10, part 4 (1968), pgs. 315–416, or those described in Chemical Reviews (1(64), Nitrones, by Jan Hamer and Anthony Macaluso, pgs. 476–483.

Various aryl ring systems with a variety of substituents may be constructed to suit the particular needs of the optical system employed in the photoimaging process. The aryl nitrones exhibit extinction coefficients of 2 to $5 \times 10^4$ liter mole$^{-1}$ cm$^{-1}$ and bleach with quantum yields in the range of 0.1 to 0.5.

For direct-step-on-the-wafer systems capable of imaging at 405 nm, the nitrones of the general structure 2 were found to be particularly useful.

Included among this subclass of p-dialkylaminoaryl nitrones are heterocyclic compounds such as 3.

Suitable binders for use in providing a spin castable mixture for formation of a photobleachable layer incorporating the aryl nitrones of formula (1) are: vinyl acetate polymers (homopolymers and copolymers) and their partially saponified products (e.g., polyvinylacetate), copolymers of styrene or its derivatives, polymers and copolymers of acrylate or methacrylate esters, acetal resins, acrylonitrile/butadiene copolymers, ethyl cellulose and other hydrocarbon-soluble cellulose ethers, cellulose propionate and other hydrocarbon-soluble cellulose esters, poly(chloroprene), poly(ethylene oxide), poly(vinylpyrrolidone).

Suitable solvents for use in providing a spin castable mixture for formation of a photobleachable layer incorporating the aryl nitrone of formula (1) are: aromatic hydrocarbons (e.g. toluene xylenes, ethyl benzene, chlorobenzene) with or without aliphatic hydrocarbons (e.g. cyclohexane), halogenated aliphatic compounds (e.g. trichloroethylene, methyl chloroform, alcohols (e.g. propanol, butanol).

The diaryl nitrone 2 where R —$CH_3CH_2$ and n=0 was found to be particularly suitable. This nitrone, referred to as α-(4-diethylaminophenyl)-N-phenylnitrone, was found to absorb strongly at 405 nm and bleaches to near transparentcy with high efficiency at the same wavelength by undergoing unimolecular cyclization to an oxaziridine. The nitrone is very soluble in solvents of moderately low polarity (e.g., toluene, ethylbenzene) and forms good films at high loading densities with a variety of polymers such as polystyrene, poly(hydroxyethylmethacrylate), poly-α-methylstyrene, poly(methyl methacrylate), polyvinylpyrrolidone, vinylpyridine/styrene copolymers and allyl alcohol/styrene copolymers. The material α-(4-diethylaminophenyl)-N-phenylnitrone has an extinction coefficient to weight ratio of 130 liters/gram-cm at 405 nm. The material was formed into a contrast enhancing layer as follows: A solution of α-(4-diethylaminophenyl)-N-phenylnitrone (5% by weight of solution) and a binder, styrene/allyl alcohol copolymer (5% by weight of solution) are dissolved in toluene. A glass substrate is spin coated to a thickness of 250 nm. The relative transmission of the sample was tested at 405 nm and was found to have the relative transmission versus time characteristic at 405 nm, shown in FIG. 3.

Figure 3:
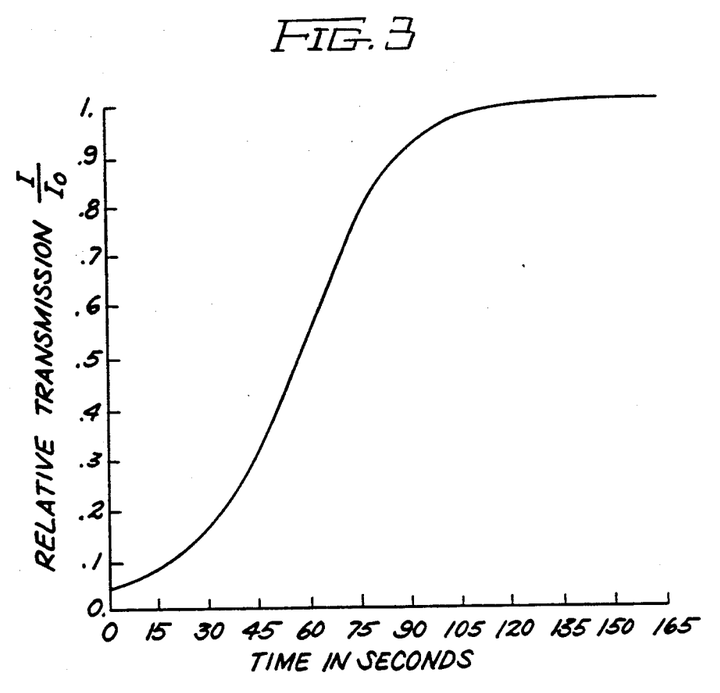
FIG. 3 is a graph of the relative transmission of a particular contrast enhancing layer as a function of time in response to the application of an incident dosage of a particular value.

The model of the bleaching process was used to calcuate the improvements in contrast as a function of exposure time for the contrast enhancing layer of FIG. 3. This is accomplished by calculating the bleaching for two representative points in a given pattern. In this example, two incident intensities that correspond to the maxima and minima of line and space grating pattern are chosen. The contrast C that these two levels of intensity correspond to can be calculated from the definition of contrast:

$$C = \frac{I_{max} - I_{min}}{I_{max} + I_{min}} \qquad (3)$$

Figure 4:
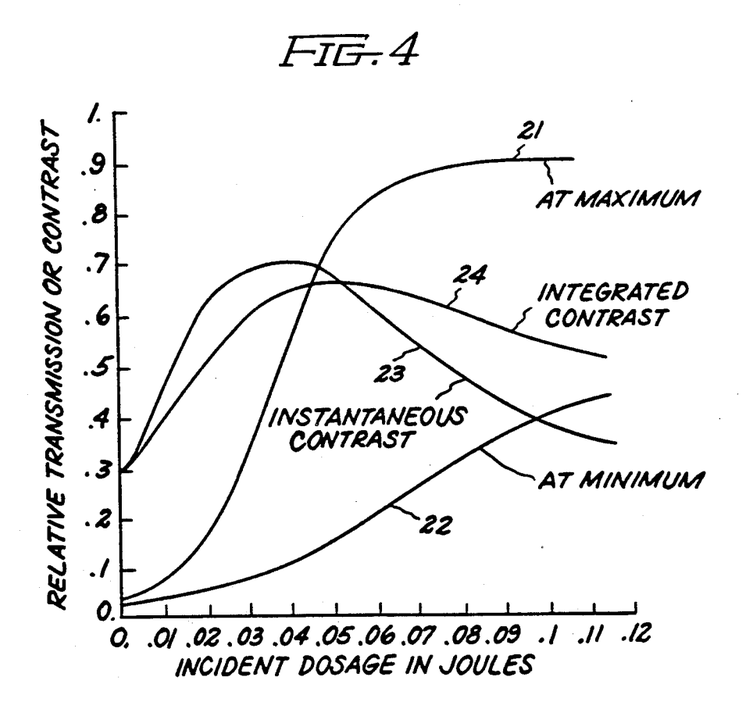
FIG. 4 shows a set of graphs showing relative transmission and contrast of an image having 30% contrast for the case of maximum and minimum transmission and the instantaneous contrast and integrated contrast produced thereby as a function of incident dosage.
Figure 5:
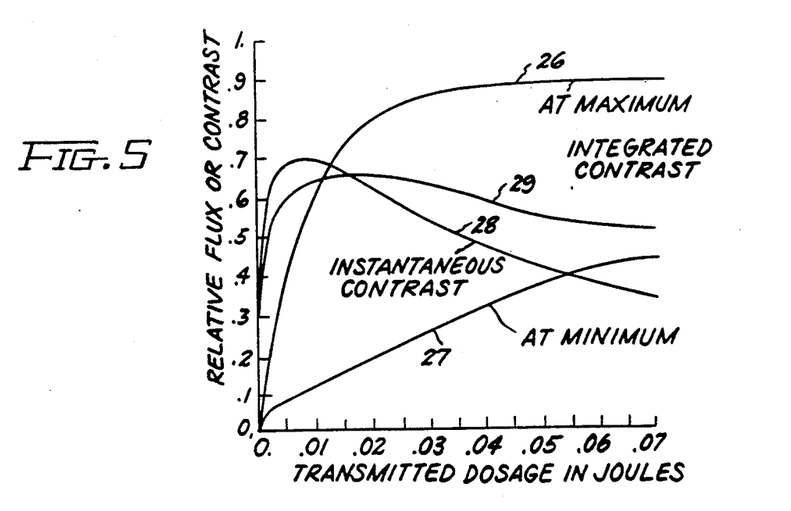
FIG. 5 shows graphs of relative transmission and contrast as a function of transmitted dosage for the graphs of FIG. 4.

Using the model of the bleaching process, the transmitted intensity as a function of incident dose for both the maxima and minima are determined. From these quantities, both the instantaneous and the integrated contrast can be calculated as a function of incident dosage. FIG. 4 shows graphs of such determinations and calculations for a 30% contrast pattern incident on the layer of the sample described above. Graph 21 shows the relative transmission at a relative maximum as a function of incident dosage in joules. Graph 22 shows the relative transmission at a minimum as a function of incident dosage. Graph 23 shows the instantaneous contrast obtained from graphs 21 and 22 using equation 3, as a function of incident dosage. Graph 24 shows the integrated contrast obtained from equation 3 using integrated values of $I_{max}$ and $I_{min}$ instead of instantaneous values. Since bleaching is a dynamic process, the contrast which results from the transmitted radiation is also a function of dosage. A more useful graphical representation is shown in FIG. 5 wherein the corresponding graphs are plotted as a function of transmitted dosage. This representation allows the degree of contrast enhancement to be estimated as a function of the sensitivity of photoresist to be used in connection with the contrast enhancing layer. Graph 26 shows relative transmission at a relative maximum as a function of transmitted dosage. Graph 27 shows relative transmission at a relative minimum as a function of transmitted dosage. Graph 28 shows the instantaneous contrast obtained from graphs 26 and 27 using equation 3, as a function of transmitted dosage. Graph 29 shows the integrated contrast obtained from equation 3 using integrated values of $I_{max}$ and $I_{min}$, as a function of transmitted dosage.

Figure 6A:
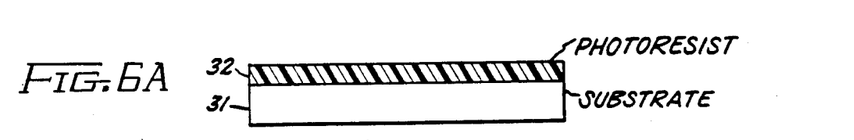
FIGS. 6A-6E show cross sections of structures representing successive steps in one method for carrying out the present invention.
Figure 6B:
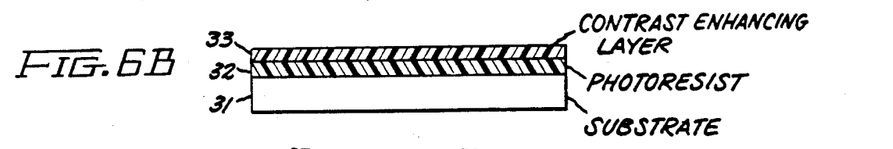
Figure 6C:
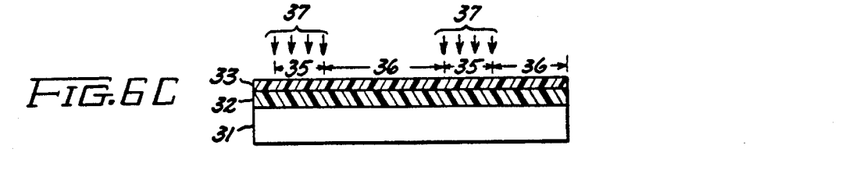
Figure 6D:
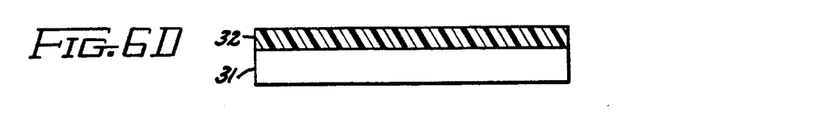
Figure 6E:
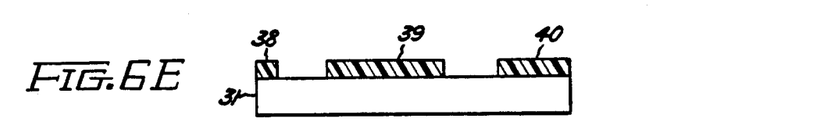

The process used for utilizing the contrast enhancing layer will now be described and thereafter the results obtained thereby will be compared with the results obtained under the same conditions but without the use of a contrast enhancing layer. Reference is now made to FIGS. 6A–6E which illustrate the various steps of the process for providing a pattern of photoresist on a suitable substrate. FIG. 6A shows a substrate 31 on which is provided a layer 32 of a suitable photoresist such as Shipley 1400 series of positive photoresists available from the Shipley Company of Newton, Mass. Such positive resists consist of a novolac resin or poly(vinylphenol), diazonaphthoquinone esters, and solvents (e.g. cellosolve acetate, xylenes). The liquid photoresist is deposited on the surface of the substrate which is then spun to provide a layer of desired thickness. After baking of the photoresist layer to remove solvent, a contrast enhancing layer 33 is provided on the surface of the photoresist. The contrasting enhancing layer 33 is constituted of a solution of a styrene/allyl alcohol copolymer binder (5% by weight of solution) and α-(4-diethylaminophenyl)-N-phenylnitrone (5% by weight of solution) in the solvent toluene. The solution is deposited on the surface of the photoresist 32, spun and thereafter baked to remove solvent to provide the layer 33 of desired thickness, as shown in FIG. 6B. The resultant structure is then exposed to a pattern of radiation consisting of illuminated regions 35 underlying the arrows 37 indicating radiation and nonilluminated regions 36 for a time to produce a contrast enhanced image in the range of dosages to which the photoresist layer is sensitive and which fully expose the layer of photoresist, as shown in FIG. 6C. Thereafter, the contrast enhancing layer 33 is removed by using a suitable stripping solvent, such as trichloroethylene, which removes the contrast enhancing layer without affecting the photoresist, as shown in FIG. 6D. Thereafter, the exposed portions of the photoresist are removed leaving retaining portions 38, 39 and 40 which are unexposed or insufficiently exposed as shown in FIG. 6E.

In order to determine the improvements in contrast threshold obtained for the composite layer of the contrast enhancing layer and photoresist in accordance with the present invention, the aforementioned photobleachable material constituted of α-(4diethylaminophenyl)-N-phenylnitrone and a styrene/allyl alcohol binder was utilized in conjunction with Shipley 1400 series of positive photoresist to fabricate various patterns. A wafer or substrate of silicon was coated with only photoresist having a thickness of 1.6 microns and another wafer of silicon was coated with a layer of photoresist 1.6 microns thick over which was coated a layer of the photobleachable material specified above to a thickness of 0.25 microns. An object consisting of an opaque line 2 microns wide, a transparent space 2 microns wide, an opaque line 0.8 microns wide and a transparent space 0.8 microns wide was imaged using the Optimetrix 10:1 projection system at 405 nanometers onto the wafer with just the layer of photoresist with a range of dosages to form a number of patterns in the photoresist and was also imaged on the wafer which included photoresist and contrast enhancing layer with a range of dosages to form a number of patterns in the photoresist. The photoresist on each of the wafers was developed to obtain the patterns of lines and spaces formed in the photoresist. Patterns produced in the wafer with just photoresist using the minimum exposure or dosage that opened the 0.8 micron space at the photoresist substrate interface were compared with the patterns produced in the wafer with photoresist and contrast enhancing layer using the minimum exposure or dosage that opened 0.8 microns space at the photoresist substrate interface. The 2.0 micron wide line and the 2.0 micron wide space, were nearly correct for both the wafer using just the photoresist and the wafer using the photoresist and the contrast enhancing layer thereon. The 0.8 micron wide line was grossly overexposed on the wafer having just the photoresist using the exposure which produced a 0.8 micron wide space in the photoresist. The 0.8 micron wide line was properly exposed producing a 0.8 wide line in the photoresist on the wafer having both photoresist and contrast enhancing layer using the exposure which produced a 0.8 wide space in the photoresist. Furthermore, the profiles of the walls of the contrast enhanced patterns were nearly vertical. The poorer resultant patterns produced in the photoresist without the contrast enhancing layer is due to the much lower aerial image contrast obtained at the output of the Optometrix projection system due to the higher spatial frequencies present in the image or pattern of radiation obtained therefrom.

While the invention has been described in connection with a particular positive photoresist, other positive and negative photoresists may be utilized. Also, while a particular thickness of photoresist and a particular thickness contrast enhancing layer were utilized in one example describing the invention, it will be understood that other thicknesses of photoresist and contrast enhancing layers may be utilized. Preferably the layer of photoresist should have a thickness less than about 3 microns and the contrast enhancing layer should have a thickness less than about 1 micron.

While in an exemplary composition of the contrast enhancing layer equal weight proportions of the photobleachable compound and the binder therefor were utilized, other proportions may be utilized, if desired.

While in connection with photoresists it was mentioned that they have a characteristic called contrast threshold, it should be noted that this characteristic is a function of conditions of usage of the photoresist as well as of the resist itself, for example, the nature of the substrate on which used and reflections therefrom.

While values of the extinction coefficient to molecular weight ratio in the unbleached state for the photobleachable compound greater than about 100 are preferred and a ratio of the extinction coefficient for the unbleached state to the extinction coefficient for the bleached state of the photobleachable compound greater than about 30 is preferred, values of the above ratios as low as about 10 would be satisfactory.

While a particular class of photobleachable compounds, neamely, the aryl nitrones, dependent on unimolecular cyclization were utilized, it will be understood that other photobleachable compounds dependent on unimolecular cyclization and on other bleaching mechanisms such as photofragmentation, for example, may be utilized in accordance with the present invention.

The aforementioned α-(4-diethylaminophenyl)-N-phenylnitrone, also set forth in Table I, was prepared by condensing p-diethylaminobenzaldehyde (18.5 g, 0.1 mole) with freshly prepared phenylhydroxylamine (11.4 g, 0.1 mole) in 40 ml of absolute ethanol at room temperature for 18 hours. Evaporation of the solvent yielded a red oil which was twice crystallized from toluene/petroleum ether to afford 13.0 g (0.05 mole) of the nitrone, mp 103°–105° C. Further recrystallization of an analytical sample raised the melting point to 110°–112° C.

Other nitrones having absorption maxima in the wavelength range of 300 to 450 nanometers are also set forth in Table I. In Table I, $\lambda_{max}$(nm) designates absorption maximum in nanometers, $\epsilon_{max}$ designates extinction coefficients at wavelength of maximum absorption, mp designates melting point in degrees Centigrade.

These other nitrones were prepared in a manner similar to the manner of preparation to the aforementioned nitrones by the condensation of the appropriate aldehydes and phenylhydroxylamines in polar solvents.

TABLE 1

$$\begin{array}{c} Ar \\ \diagdown \\ CH=N^{+} \\ \diagdown \\ Ar' \end{array} \begin{array}{c} {}^{-}O \\ \diagup \\ \phantom{CH=N} \end{array}$$

| Ar | Ar' | $\lambda_{max}$(nm) | $\epsilon_{max}$ | mp (°C.) |
|---|---|---|---|---|
| α-(4-diethylaminophenyl)-N-phenylnitrone | | | | |
| 1) (CH₃CH₂)₂N—⟨phenyl⟩— |  | 388 | 41,000 | 110–112 |

α-(4-diethylaminophenyl)-N-(4-chlorophenyl)nitrone

TABLE 1-continued $$\underset{Ar'}{\overset{Ar}{\diagdown}}CH=\overset{+}{\underset{Ar'}{N}}\diagup^{-O}$$

| | Ar | Ar' | $\lambda_{max}$(nm) | $\epsilon_{max}$ | mp (°C.) |
|---|---|---|---|---|---|
| 2) |  |  | 398 | 42,500 | 176–179 |
| 3) | α-(4-diethylaminophenyl)-N-(3,4-dichlorophenyl)nitrone  |  | 409 | 43,700 | 154–157 |
| 4) | α-(4-diethylaminophenyl)-N-(4-ethoxycarbonylphenyl)nitrone  |  | 418 | 31,300 | 107–109 |
| 5) | α-(4-diethylaminophenyl)-N-(4-acetylphenyl)nitrone  |  | 424 | 27,000 | 115 |
| 6) | α-(4-dimethylaminophenyl)-N-(4-cyanophenyl)nitrone  |  | 420 | 33,000 | 202–203 |
| 7) | α-(4-methoxyphenyl)-N-(4-cyanophenyl)nitrone  |  | 368 | 13,000 | 181–182 |
| 8) | α-(9-julolidinyl)-N-phenylnitrone  |  | 405 | 38,000 | 132–133 |
| 9) | α-(9-julolidinyl)-N-(4-chlorophenyl)nitrone  |  | 420 | 36,600 | 99–103 |
| 10) | α-[2-(1,1-diphenylethenyl)]-N-phenylnitrone  |  | 366 | 27,800 | 140–142 |

TABLE 1-continued

| | Ar | Ar' | $\lambda_{max}$(nm) | $\epsilon_{max}$ | mp (°C.) |
|---|---|---|---|---|---|
| 11) α-[2-(1-phenylpropenyl)]-N-phenylnitrone |  | | 340 | 19,000 | 468 |

In the method of the invention the photobleachable layer is in the form of an in situ mask on the layer of photoresist. The formation of such a composite structure has a number of advantages. The photobleachable layer conforms to the surface of the layer of photoresist and avoids the formation of gaps between the high points of the surfaces of the layer of photobleachable material and the layer of photoresist. Such gaps would be formed when the two layers are formed on separate supports and then brought together. Such gaps would be highly detrimental to the resolution of any image formed in the photoresist particularly when the features to be imaged are of the order of a few microns and also when the depth of field of the projection system is a few microns. Also, bringing a layer of photobleachable material into contact with a layer of photoresist and thereafter separating them runs the risk of having pieces of one layer adhering to the other layer thereby damaging the layers of photoresist.

While in describing the invention in an exemplary embodiment, the contrast enhancing layer was situated in contact with the layer of the photoresist, the contrast enhancing layer could have been spaced apart from the layer of the photoresist, if desired, for example, by a thin conformal layer of neutral material formed in situ.

While the invention has been described in specific embodiments, it will be understood that modifications such as those described above may be made by those skilled in the art, and it is intended by the appended claims to cover all such modifications and changes as fall within the true spirit and scope of the invention.

What is claimed is:

1. A composite useful in making microelectronic circuits comprising a silicon wafer, a photoresist formed on the surface of the silicon wafer and a photobleachable layer that has been formed in situ upon the surface of the photoresist opposite the silicon wafer by spin casting a mixture thereon comprising by weight
   (A) 100 parts of organic solvent,
   (B) 1 to 30 parts of inert organic polymer binder, and
   (C) 1 to 30 parts of an ultraviolet radiation sensitive photobleachable organic compound.

2. A composite in accordance with claim 1, where the photobleachable layer has a thickness of less than about 1 micron and the photoresist has a thickness of less than about 3 microns.

3. A composite in accordance with claim 1, where the photobleachable organic compound has an extinction coefficient to molecular weight ratio in liters per gram/cm in the unbleached state greater than about 10.

4. A composite in accordance with claim 1, where the photobleachable organic compound is a photoisomerizable compound.

5. A composite in accordance with claim 1, where the photobleachable organic compound is a photofragmentable compound.

6. A composite in accordance with claim 1, where the photobleachable organic compound is an arylnitrone.

7. A composite in accordance with claim 1, where the photobleachable layer is formed by spin casting a mixture upon the surface of the photoresist which comprises by weight
   (A) 100 parts of organic solvent,
   (B) 5 to 15 parts of inert polymer binder, and
   (C) 5 to 15 parts of photobleachable organic compound.

8. A composite in accordance with claim 1, where the photobleachable layer has an absorption maximum in the range of 300 to 450 nanometers.

* * * * *